United States Patent [19]
Barber et al.

[11] Patent Number: 5,633,997
[45] Date of Patent: May 27, 1997

[54] USER INTERFACE FOR SPECTROMETER

[75] Inventors: Luther L. Barber, Needham; Mark L. Olson, Framingham; Paul V. Carter, Brighton, all of Mass.

[73] Assignee: Bio-Rad Laboratories, Cambridge, Mass.

[21] Appl. No.: 453,709

[22] Filed: May 30, 1995

Related U.S. Application Data

[63] Continuation-in-part of Ser. No. 333,955, Nov. 3, 1994, Pat. No. 5,579,462.

[51] Int. Cl.$^6$ ............................................. G06F 15/00
[52] U.S. Cl. ............................................. 395/140
[58] Field of Search .................... 395/139, 140, 395/155, 161; 345/133, 134

[56] References Cited

U.S. PATENT DOCUMENTS

| | | | |
|---|---|---|---|
| 5,283,867 | 2/1994 | Bayley et al. | 395/164 |
| 5,462,438 | 10/1995 | Becker et al. | 434/430 |

OTHER PUBLICATIONS

"Grams/38 Level III Database Operations", Galactic Industries Corporation, 1991.

"Subtraction", Grams (brochure), Galactic Industries Corporation (Jun., 1992).

"Quick IR+ User's Guide, Version 1.0", OMNIC FT-IR Software, Nicolet Instrument Corporation (1994).

*Primary Examiner*—Phu K. Nguyen
*Attorney, Agent, or Firm*—Townsend and Townsend and Crew LLP

[57] ABSTRACT

A method for graphically forming a difference spectrum from a sample spectrum and a reference spectrum on a computer system includes displaying an initial difference spectrum on the display the initial difference spectrum being equal to the sample spectrum, selecting a data point in the initial difference spectrum, having an associated wave number, with a relative pointing device on the display, moving the data point a measurable amount on the display with the relative pointing device, determining a scaling factor in response to the measurable amount and to a data point in the reference spectrum having the same associated wave number, scaling each data point in the reference spectrum by the scaling factor to form a scaled reference spectrum, determining the difference spectrum between the sample spectrum and the scaled reference spectrum, and displaying at least a portion of the difference spectrum on the display.

21 Claims, 16 Drawing Sheets

| NAME | SPECTRUM | STRUCTURE |
|------|----------|-----------|
| BENZENE | | |
| ETHANE | | |
| FRED | | |
*FIG. 10*
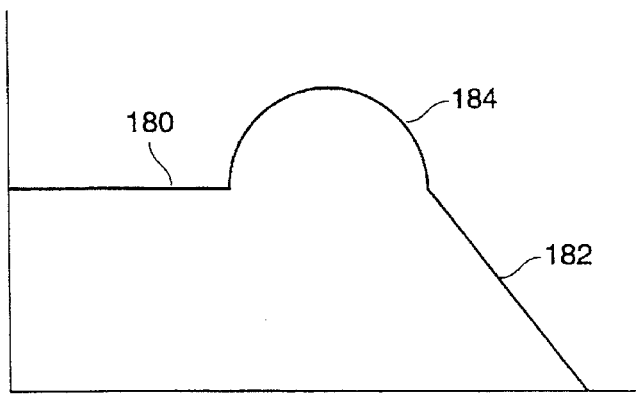
*FIG. 11*
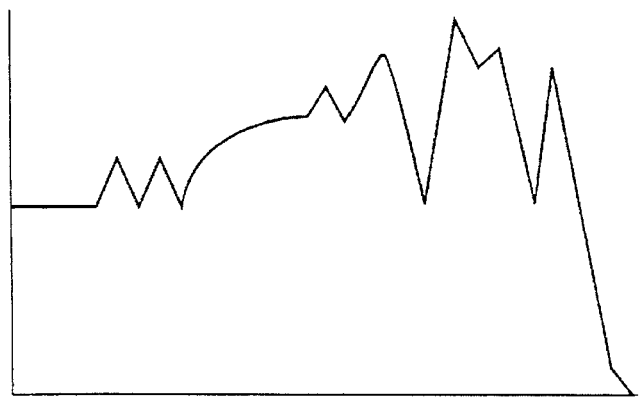
*FIG. 12*

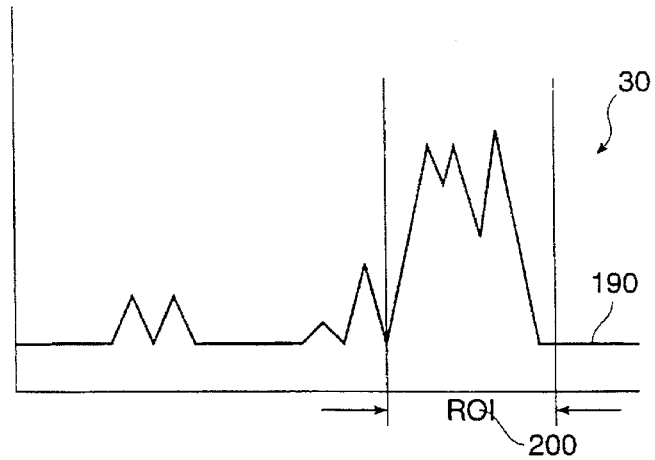
FIG. 13A
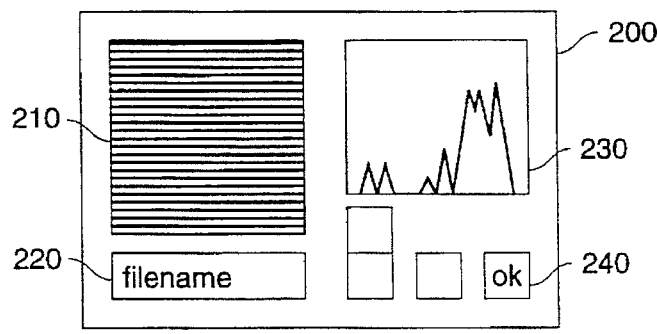
FIG. 13B
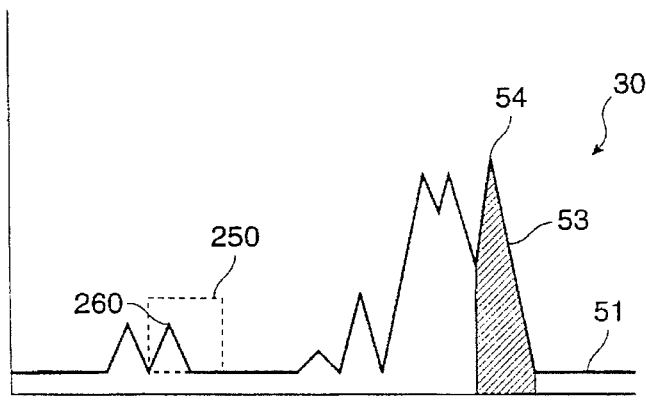
FIG. 14
FIG. 15

USER INTERFACE FOR SPECTROMETER

CROSS-REFERENCE TO RELATED APPLICATIONS

The present invention is a continuation-in-part of application Ser. No. 08/333,955 filed Nov. 3, 1994, now U.S. Pat. No. 5,579,462.

BACKGROUND OF THE INVENTION

The present invention relates generally to graphical display of spectral data, and more specifically to user interface enhancements that facilitate the examination and manipulation of such data.

Spectral analysis is often used to determine the qualitative or quantitative composition of a sample. Typical spectral data consist of the absorbance of the sample or specimen at different wavelengths or frequencies of light. Absorbance data are typically plotted against inverse wavelength (a measure of frequency referred to as wavenumber), with the resulting graph being referred to as a spectrum. Also note that while the discussion of typical usage is appropriately in terms of absorbance versus wavenumber, many of the same manipulations are applicable to a number of other y units (such as %Transmittance, reflectance, Volts) and x units (such as optical retardation of an interferogram, microns, electron Volts).

In order to interpret spectrum, raw data collected from a sample may require additional manipulations:

(1) Specific sampling techniques affect raw spectral data in known, predictable ways; manipulations can convert the data into a sampling-independent standard form.
(2) Sample preparation and sampling techniques may introduce artifacts, and data manipulations may be applied to correct these.
(3) Many samples are mixtures, and manipulations are required to determine the spectrum and concentrations of the individual compounds present.

In order to eliminate known artifacts and eliminate known components from a sample compound, the data points of the sample spectrum are commonly modified. In one method, each spectral data point in the sample spectrum S, is modified by a corresponding data point representing a known sample compound, in the form of a reference spectrum R. The resulting modified spectrum Z, is related to S and R by equation (1), where a and b are scalar values.

$$Z = S - (a*R) + b \quad (1)$$

Typically, the user inputs a value for "a" and "b" and the processor calculates the modified spectrum Z. After observing the results of the modified spectrum Z, the user can again modify the values for "a" and "b" and review the new spectrum Z. This process is repeated until the user is satisfied with the appearance of the modified spectrum Z. A similar modification of a sample spectrum is used in determining the composition of the sample or is used in adjusting the baseline offset of the spectrum.

The user often magnifies portions of the sample spectrum to concentrate his analysis. Current systems allow the user the ability to increase or decrease the amount of the spectrum, i.e. the range of wave numbers, that is displayed to the user.

SUMMARY OF THE INVENTION

The present invention provides user interface enhancements in a computerized spectral analysis system that allow the user to directly manipulate spectral representations on the display in a highly intuitive and interactive manner. The user is able, with a pointing device, to directly select a portion of the spectrum for display and to directly perform graphic manipulation of the spectrum, such as spectral subtraction.

According to a preferred embodiment of the invention, a method of displaying a spectrum on a computer system having a display and a graphical input device includes the steps of displaying a reduced size view of the spectrum in a radar window on the display; displaying an overlay window on top of the reduced view; displaying a portion of the spectrum corresponding to the portion of the reduced view bounded by the overlay window in a detailed window on the display; and thereafter displaying a resized and/or repositioned overlay window on top of the reduced view in response to input from the graphical input device, the resized and/or repositioned window bounding a second portion of the reduced view; and displaying a second portion of the spectrum corresponding to the second portion of the reduced view in the detailed window on the display.

According to another embodiment of the invention, a method for graphically manipulating a sample spectrum on a computer system includes the steps of displaying at least a portion of a difference spectrum on the display, the difference spectrum being the mathematical difference between the sample spectrum and a scaled reference spectrum, the scaled reference spectrum being a reference spectrum scaled by a scaled value; and updating the scaled value in response to graphical manipulation of the difference spectrum by the graphical input device.

Further understanding of the nature and advantages of the invention may be realized by reference to the remaining portions of the specification and drawings. In the drawings, similarly numbered items represent the same or functionally equivalent structure.

BRIEF DESCRIPTION OF THE DRAWINGS

FIG. 10 illustrates the result of searching the sample spectrum in FIG. 2 against a library of known spectrum;

FIGS. 11 and 12 illustrate the definition of a portion of a baseline offset as a function of wavenumber and the resulting spectrum;

FIG. 13A illustrates a display of a portion of a spectrum on a detailed window;

FIG. 13B illustrates the result of an automatic subtraction based upon a region of interest;

FIG. 14 illustrates retrieving a previously scanned sample spectrum from a disk drive;

FIG. 15 illustrates the peak mode;

DESCRIPTION OF THE PREFERRED EMBODIMENT

System Overview

Figure 1:
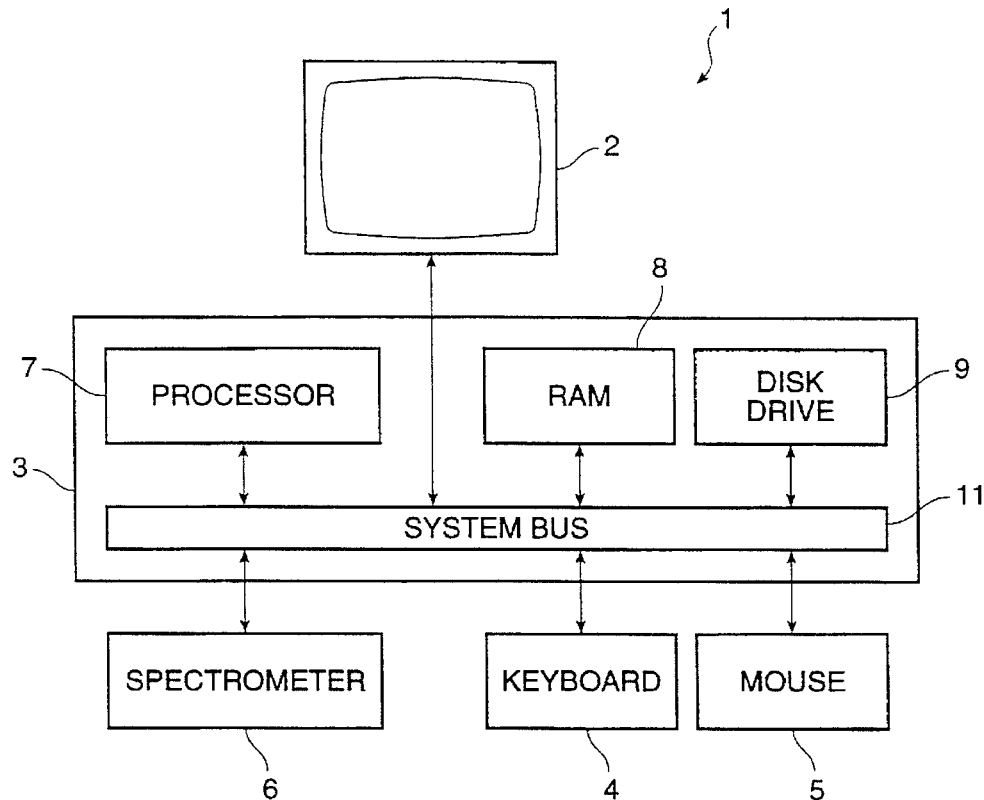
FIG. 1 is a block diagram of a computer system used to execute the present invention.

FIG. 1 is a block diagram of a system 1 according to a preferred embodiment of the present invention. System 1 includes a monitor 2, a computer 3, a keyboard 4, a mouse 5, and a spectrometer 6. Computer 3 includes familiar computer components such as a processor 7, and memory storage devices, such as a random access memory (RAM) 8, a disk drive 9, and a system bus 11 interconnecting the above components. Mouse 5 is but one example of a graphical input device, also known as a pointing device, a trackball is another.

In a preferred embodiment, System 1 includes an IBM PC compatible personal computer, running Windows-NT operating system by Microsoft Corporation and an infra-red spectrometer Model Number FTS 60A from Bio-Rad Laboratories, Inc., and Win-IR Pro software, currently under development by Bio-Rad Laboratories, Inc.

FIG. 1 is representative of but one type of system for embodying the present invention. It will be readily apparent to one of ordinary skill in the art that many system types and configurations are suitable for use in conjunction with the present invention.

Display Overview

Figure 2:
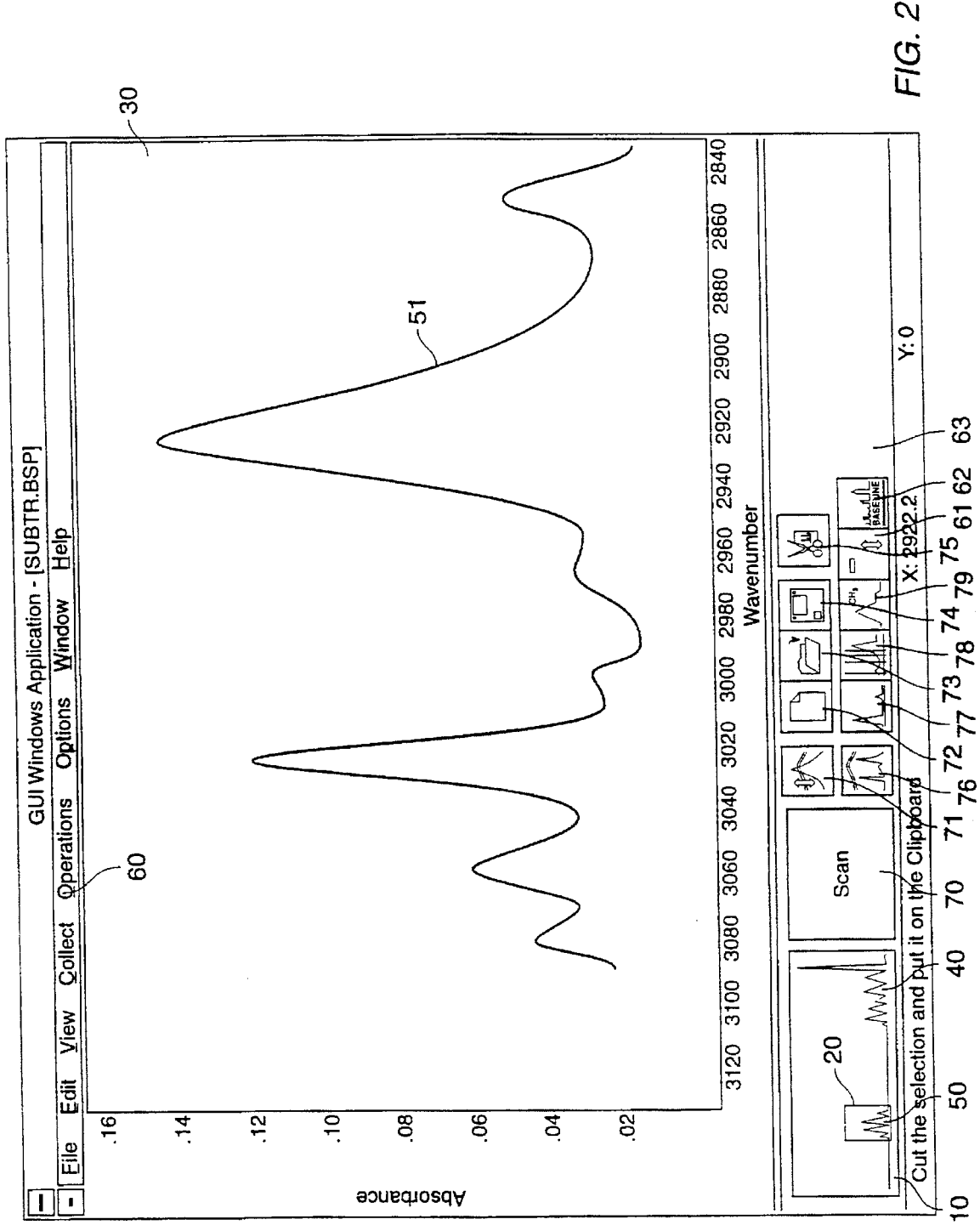
FIG. 2 illustrates one embodiment of the present invention.

FIG. 2 illustrates the display of one embodiment of the present invention, as it would appear on monitor 2. A typical display includes a "radar" window 10 having an overlay window 20, and a detailed window 30. Radar window 10 displays a full range of a spectrum 40, overlay window 20 bounds a portion 50 of spectrum 40, and detailed window 30 displays portion 50 (labeled 51 for convenience). Spectrum 40 is a display of data for a sample spectrum, and can be displayed in a user-selected color.

In accordance with standard user interfaces, a menu bar 60, and command buttons 70–79 and 61–63 are included on the display to provide function capability to the user. In a preferred embodiment of the present invention, command button 70 is a scan button; command button 71 is a automatic vertical scaling button; command button 72 is a new document button; command button 73 is an open folder; command button 74 is a disk select button; command button 75 is a clipboard button; command button 76 is an automatic ranging button; command button 77 is an overlay window button; command button 78 is a spectrum mask button; command button 79 is a peak mode button; command button 61 is a graphic subtraction mode button; command button 62 is a baseline correction button; and command button 63 is a reference definition button.

In a preferred embodiment, the user first selects command button 70, the scan button, or one of commands in menu bar 60 to initiate scanning of the sample in spectrometer 6. The spectrometer 6 scans a sample (not shown) and processor 7 stores the absorbance data of the sample at different wave numbers in memory 8. The absorbance data versus the wave numbers collectively form the sample spectrum. A sample spectrum can be retrieved from disk drive 9 and loaded into memory 8 by selecting a combination of command buttons 73–74.

Once the data are stored in memory 8 from a scan or from disk drive 9, the processor calculates a spectrum that spans a predefined range of wave numbers or a range of wave numbers having associated absorbance data. This spectrum is then displayed in radar window 10 on the display and denoted the spectrum 40.

In the preferred embodiment, absorbance data is plotted on the vertical axis and wavenumber data is plotted in the horizontal axis.

Next, the processor superimposes overlay window 20 upon radar window 10. The portion of spectrum 40 that is bounded by overlay window 20 defines portion 50. The processor retrieves the spectrum data for portion 50 and displays this data labeled portion 51 in detailed window 30 on the display. Since radar window 10, in one embodiment, occupies a smaller portion of the display than detailed window 30, spectrum 40 is also referred to as a reduced view of the spectrum.

Radar Window Manipulation

Figure 3B:
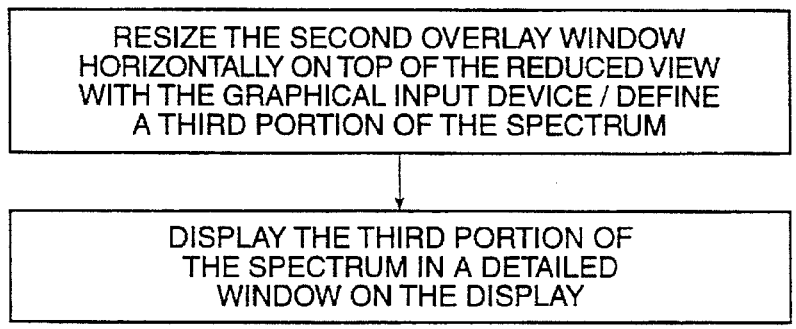
FIG. 3B a flow diagram of another embodiment of the process of utilizing an overlay window in the radar window.
Figure 3C:
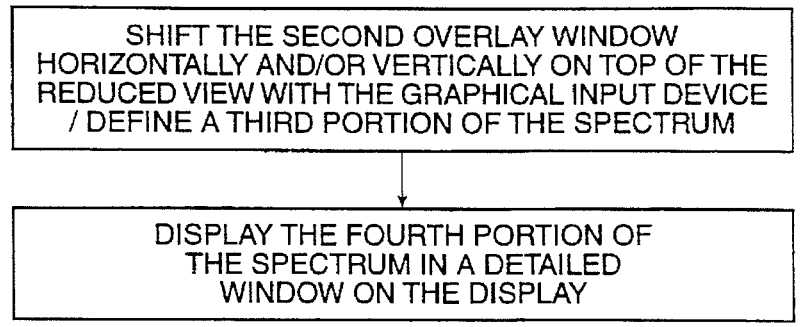
FIG. 3C is a flow diagram of another embodiment of the process of utilizing an overlay window in the radar window.
Figure 3A:
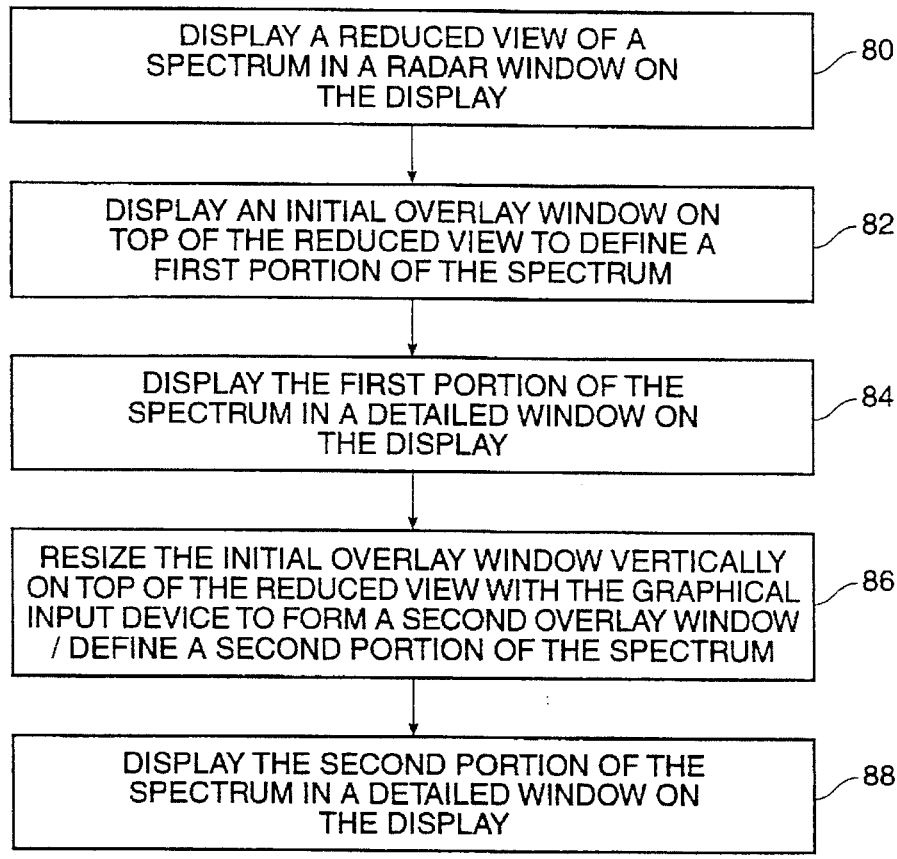
FIG. 3A is a flow diagram of one embodiment of the process and result of utilizing an overlay window in the radar window.

FIG. 3A is a flow diagram of one embodiment of the process and result of utilizing an overlay window in the radar window. A reduced view of spectrum is displayed to the user in the radar window on the display (step 80). The processor generates an initial overlay window in the radar window that bounds and defines a first portion of the spectrum (step 82). The first portion of the spectrum is then displayed to the user in the detailed window (step 84). Using a graphical input device, such as mouse 5, a user vertically resizes the overlay window in the radar window so that the overlay window bounds and defines a second portion of the spectrum (step 86). The second portion of the spectrum is then displayed to the user in the detailed window (step 88).

FIG. 3B is a flow diagram of another embodiment of the process of utilizing an overlay window in the radar window.

In addition to steps 80–88 in FIG. 3A, the user may use the graphical input device to horizontally resize the overlay window in the radar window so that the overlay window bounds and defines a third portion of the spectrum (step 90). In this case, the third portion of the spectrum is then displayed to the user in the detailed window (step 92).

FIG. 3C is a flow diagram of another embodiment of the process of utilizing an overlay window in the radar window. In addition to steps 80–88 in FIG. 3A, the user may use the graphical input device to shift the overlay window horizontally and/or vertically in the radar window so that the overlay window bounds and defines a fourth portion of the spectrum (step 94). In this case, the fourth portion of the spectrum is then displayed to the user in the detailed window (step 96). In the preferred embodiment of the present invention, the portion of the spectrum displayed in the detailed window on the display is dynamically updated as the overlay windows are resized and/or repositioned.

Figure 4A:
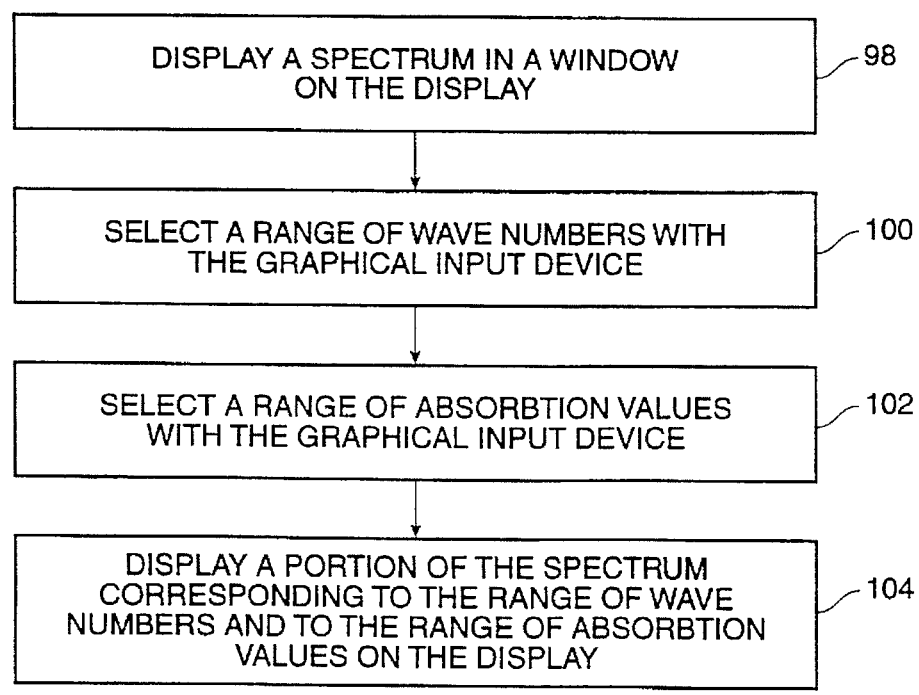
FIG. 4A is a flow diagram of an embodiment of the process of displaying a user-selected portion of a spectrum.

FIG. 4A is a flow diagram of an embodiment of the process of displaying a user-selected portion of a spectrum selected in the reduced display. A spectrum is first displayed to the user on the display (step 98). In the preferred embodiment of the present invention, the user simultaneously selects a range of wave numbers with the graphical input device on the display (step 100) and selects a range of absorbance values also with the graphical input device on the display (step 102). The user selects the respective ranges with the graphical input device, such as mouse 5, using well known techniques such as clicking upon a base value, and dragging mouse 5 until the desired ranges are achieved. Once the respective ranges are defined by the user, a portion of the spectrum corresponding to the respective ranges is displayed to the user (step 104).

Figure 4B:
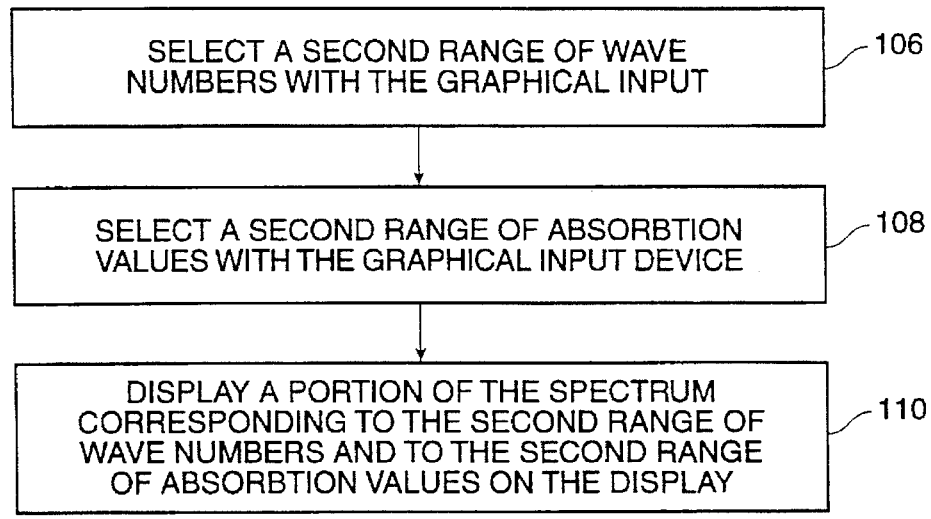
FIG. 4B is a flow diagram of another embodiment of the process of displaying a user-selected portion of a spectrum.

FIG. 4B is a flow diagram of another embodiment of the process of displaying a user-selected portion of a spectrum. In addition to the steps 98–104 in FIG. 4A, the user selects a second range of wave numbers on the display (step 106) and the user selects a second range of absorbance values on the display (step 108), again using well known techniques such as clicking upon a base value, and dragging mouse 5 until the desired ranges are achieved. In the preferred embodiment of the present invention these steps can occur simultaneously. Once the respective second ranges are defined by the user, a portion of the spectrum corresponding to the respective second ranges is displayed to the user (step 110).

In a preferred embodiment, in the detailed window, the user can "zoom in" on a portion of spectrum 51 by directly defining a region of spectrum 51 in detailed window 30 with the graphical input device in the same manner as overlay window 20. In response, overlay window 20 is updated to reflect the region of the spectrum displayed in detailed window 30.

Figure 5A:
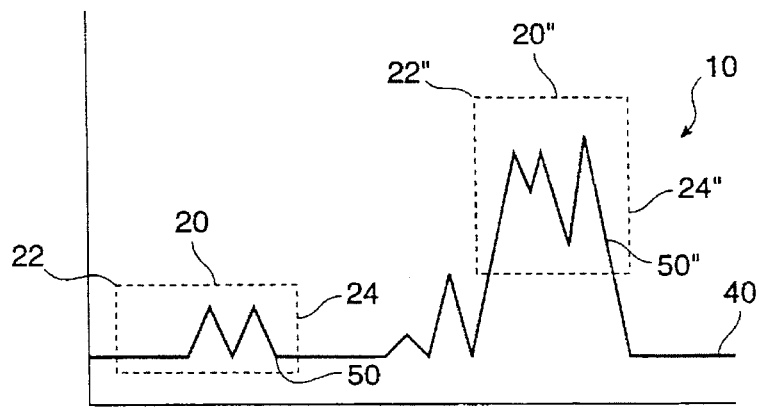
FIG. 5A schematically illustrates moving and stretching of the overlay window on a full spectrum.

FIG. 5A illustrates schematically the moving and stretching of overlay window 20 from a first position to a second position in radar window 10. The overlay window at the second position is denoted 20". Overlay window 20 includes a horizontal side 22 and a vertical side 24, and overlay window 20" includes a horizontal side 22" and a vertical side 24". Overlay window 20 bounds portion 50 and overlay window 20" bounds a portion 50" of the spectrum 40.

In a preferred embodiment, the user employs a graphical input device such as a mouse to manipulate overlay window 20 using well known methods such as pointing, clicking, and dragging a pointer on the display. Specifically with mouse 5, the user independently varies the horizontal location, the vertical location, and the size of overlay window 20 within radar window 10.

The user, clicking the pointer within overlay window 20 and dragging the pointer in the horizontal and vertical direction within radar window 10, shifts the position of overlay window 20 within radar window 10. The shift in the overlay window 20 is reflected in detailed window 30 by the processor displaying different wavenumber data and absorbance data, although the processor maintains the range of wave numbers (horizontal range) and the range of absorbance values (vertical range).

The user, clicking the pointer on vertical side 24 and dragging the pointer in the horizontal direction within radar window 10, increases or decreases the size of horizontal side 22 of overlay window 20 within radar window 10. The change in size of horizontal side 22 is also reflected in detailed window 30 by the processor increasing or decreasing the range of wave numbers displayed in detailed window 30. Similarly, the user clicking the pointer on horizontal side 22 and dragging the pointer in the vertical direction within radar window 10, increases or decreases the size of vertical side 24 of overlay window 20 within radar window 10. The change in size of vertical side 24 is also reflected in the detailed window 30 by the processor increasing or decreasing the range of absorbance values displayed in detailed window 30.

Figure 5B:
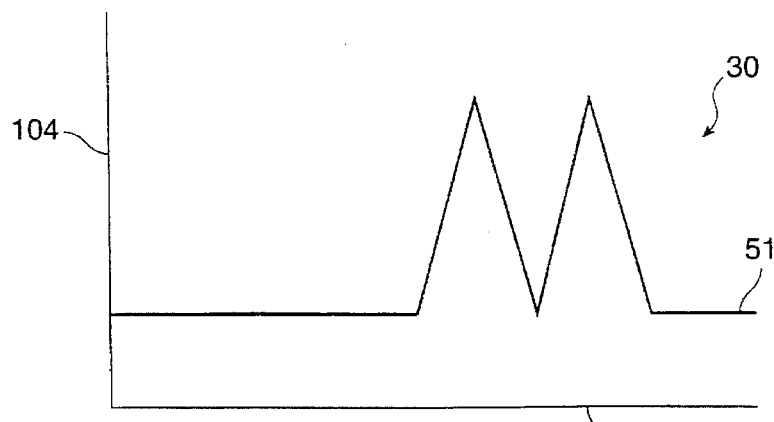
FIG. 5B schematically illustrates the detailed window corresponding to the overlay window at a first position in FIG. 5A.

FIG. 5B illustrates schematically detailed window 30 corresponding to overlay window 20 in FIG. 5A. Detailed window 30 includes a horizontal scale 102 representing a range of wave numbers, a vertical scale 104 representing a range of absorbance values, and portion 51 of spectrum 40.

In operation, overlay window 20 on spectrum 40 defines portion 50 of spectrum 40. Based upon the size and position of horizontal side 22 and the size and position of vertical side 24 of FIG. 5A, the processor determines horizontal scale 102 and vertical scale 104, respectively for detailed window 30. The processor then displays portion 50, labeled 51 for convenience, in detailed window 30.

Figure 5C:
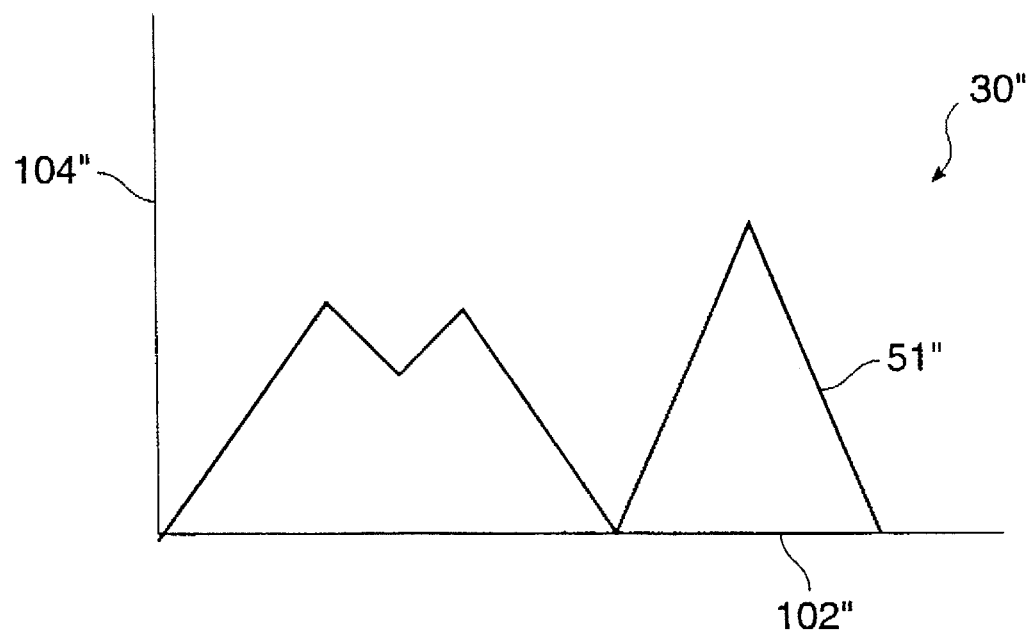
FIG. 5C schematically illustrates the detailed window corresponding to the overlay window at a second position in FIG. 5A.

FIG. 5C illustrates schematically detailed window 30" corresponding to overlay window 20" in FIG. 5A. Detailed window 30" includes a horizontal scale 102" representing a range of wave numbers, a vertical scale 104" representing a range of absorbance values, and portion 51" of spectrum 40.

In a preferred embodiment, the user uses mouse 5 to select overlay window 20" in FIG. 5A, to shift overlay window 20 horizontally and vertically, and to resize horizontal side 102 and vertical side 104 to become overlay window 20". Overlay window 20" on spectrum 40 defines portion 50" of spectrum 40. Based upon the size and position of horizontal side 22" and the size and position of vertical side 24" in FIG. 5A, the processor determines horizontal scale 102" and vertical scale 104", respectively for detailed window 30. The processor then displays portion 51", in detailed window 30".

In a preferred embodiment, the user uses mouse 5 to draw a new overlay window 20" in FIG. 5A. Overlay window 20" on spectrum 40 defines portion 50" of spectrum 40. Based upon the size and position of horizontal side 22" and the size and position of vertical side 24" in FIG. 5A, the processor determines horizontal scale 102" and vertical scale 104", respectively for detailed window 30. The processor then displays portion 51", in detailed window 30".

Radar Window Refinements

Figure 6:
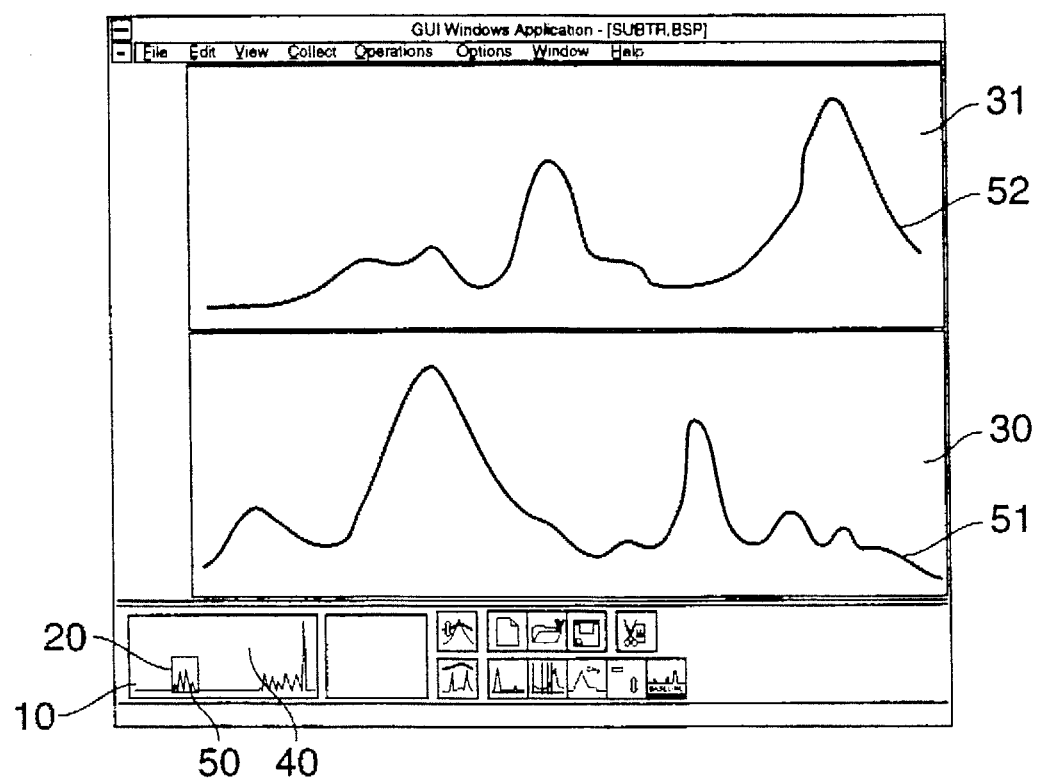
FIG. 6 illustrates a display of another embodiment of the present invention.

FIG. 6 illustrates a display of another embodiment of the present invention. The examples in FIGS. 2 and 5A–5C illustrate the use of one radar window 10 with one detailed window 30 on a display. In a preferred embodiment, however, more than one detailed window is displayed to the user at the same time on the display, such as detailed window 30 and a second detailed window 31. Thus, a typical monitor display includes radar window 10 having an overlay window 20 and detailed windows 30 and 31. Radar window 10 displays a spectrum 40 and overlay window 20 bounds portion 50 of spectrum 40, detailed window 30 displays a portion of spectrum 40 labeled 51, and detailed window 31 displays a portion 52 of a second spectrum (not shown). Spectrum 40 and the second spectrum are displays of spectrum data.

Multiple detailed windows such as 30 and 31 are used, for example, when the user wants to perform a visual comparison of two or more different spectrum at the same time. Although it is possible to have as many radar windows as there are detailed windows on the display, because of the limited display area on monitor 2, in the preferred embodiment, only one radar window 10 is provided.

In the preferred embodiment, radar window 10 displays the spectrum associated with an "active" detailed window and an "active" spectrum. The "active" spectrum is the spectrum upon which the processor can perform operations, such as saving, modifying, etc. To "activate" a spectrum and "activate" a detailed window, the user uses a graphic input device such as mouse 5 and clicks a pointer within one of the detailed windows on the display. In FIG. 6 the "active" spectrum is spectrum 40 and the "active" detailed window is window 30.

The user can override the above described functionality of overlay window 20 by selecting command button 71 or command button 76, illustrated in FIG. 2. Selecting command button 71 automatically re-scales vertical scale 104 such that the vertical range of portion 51 is enhanced, while keeping horizontal scale 102 relatively fixed. Enhancement includes increasing or decreasing the range of absorbance values in vertical scale 104.

Selecting command button 76 automatically re-scales vertical scale 104 and horizontal scale 102 such that the full range of spectrum 40 is displayed in detailed window 30. This includes increasing or decreasing the range of absorbance values in vertical scale 104 and increasing or decreasing the range of wave numbers in the horizontal scale 102. To return to utilizing and manipulating overlay window 20 in radar window 10, the user selects command button 77.

Graphic Manipulation–Subtraction

Subtraction of a reference spectrum from a sample spectrum allows the user, for example, to eliminate spectral artifacts from the sample spectrum or to determine the composition of the sample spectrum. The result of the spectral subtraction is a difference spectrum.

Figure 7:
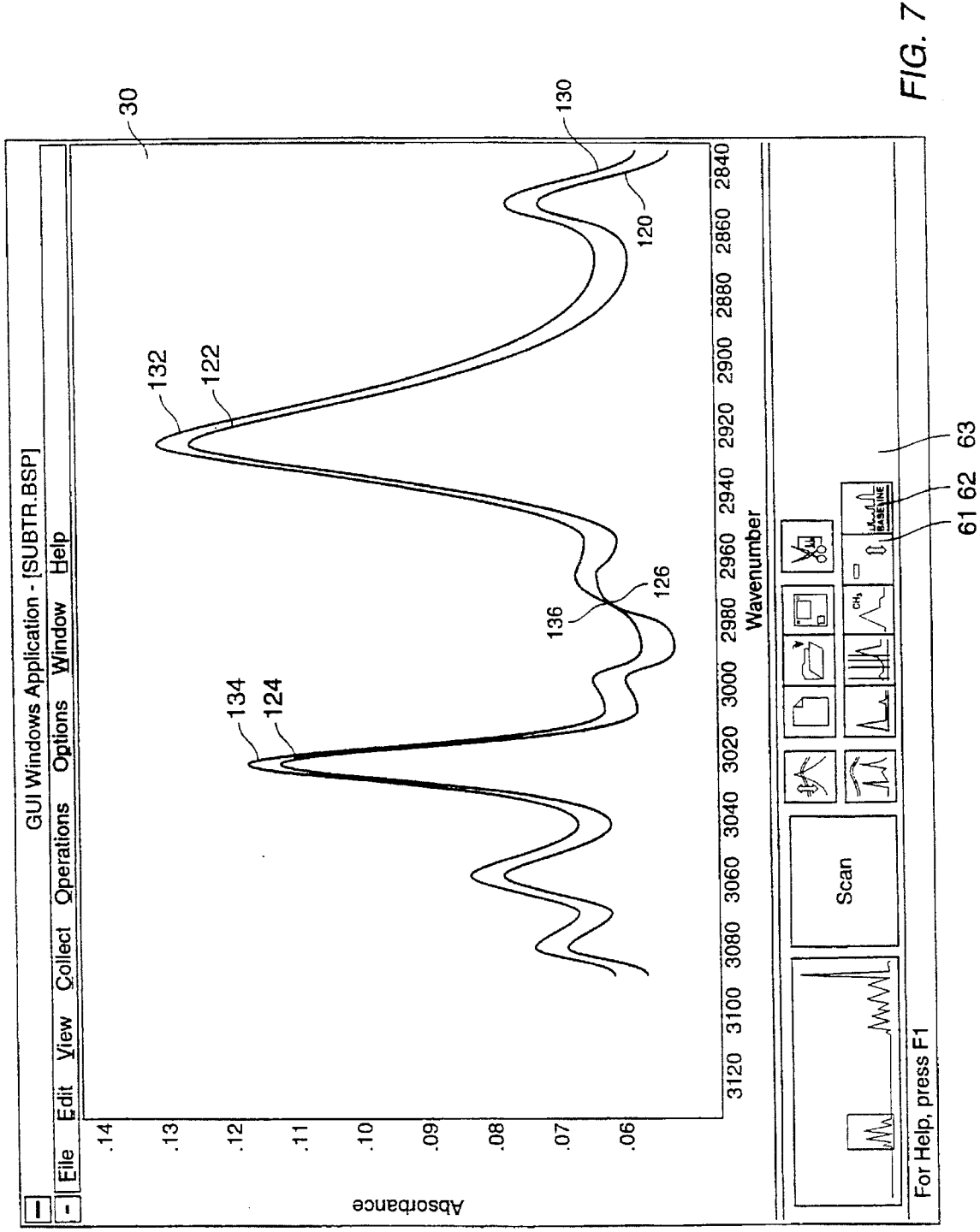
FIG. 7 illustrates the display of a portion of a sample spectrum and a portion of a reference spectrum in a detailed window.

FIG. 7 illustrates the display of portion 120 of a sample spectrum and a portion 130 of a reference spectrum over the same wavenumber range on detailed window 30. These portions 120 and 130 can be displayed in two different user selected colors to avoid any confusion between the spectra. The wavenumber ranges of the two spectrum are determined by overlay window 20 in radar box 10. Portion 120 includes points 122, 124, 126, and portion 130, includes points 132, 134, and 136. The reference spectrum includes spectral data from known reference materials such as pure compounds and mixtures.

In a preferred embodiment, the user scans a sample spectrum using spectrometer 6 (or retrieves a previously scanned spectrum from disk drive 9) and then selects command button 61 to enter the graphic subtraction mode. Once in the graphic subtraction mode, the user retrieves a reference spectrum from disk drive 9.

Using overlay window 20 in radar window 10 to survey the sample spectrum and the reference spectrum, the user typically determines which portions of the sample spectrum and the reference spectrum appear similar in shape. If the sample spectrum does not have waveform characteristics similar to that of the reference spectrum, the user may decide to skip this reference spectrum and load a new reference spectrum from disk drive 9. If the sample spectrum has similar characteristics to the reference spectrum, the user may decide to perform the graphical subtraction. In the example in FIG. 7, the sample spectrum includes regions surrounding points 122 and 124 which are similar in shape to regions surrounding points 132 and 134 of the reference spectrum, respectively.

Once the user determines a reference spectrum to use for the graphical subtraction, the processor generates a difference spectrum between the two spectrum. The difference spectrum can be displayed in a third user selected color to visually distinguish the difference spectrum from the other spectra.

Figure 8:
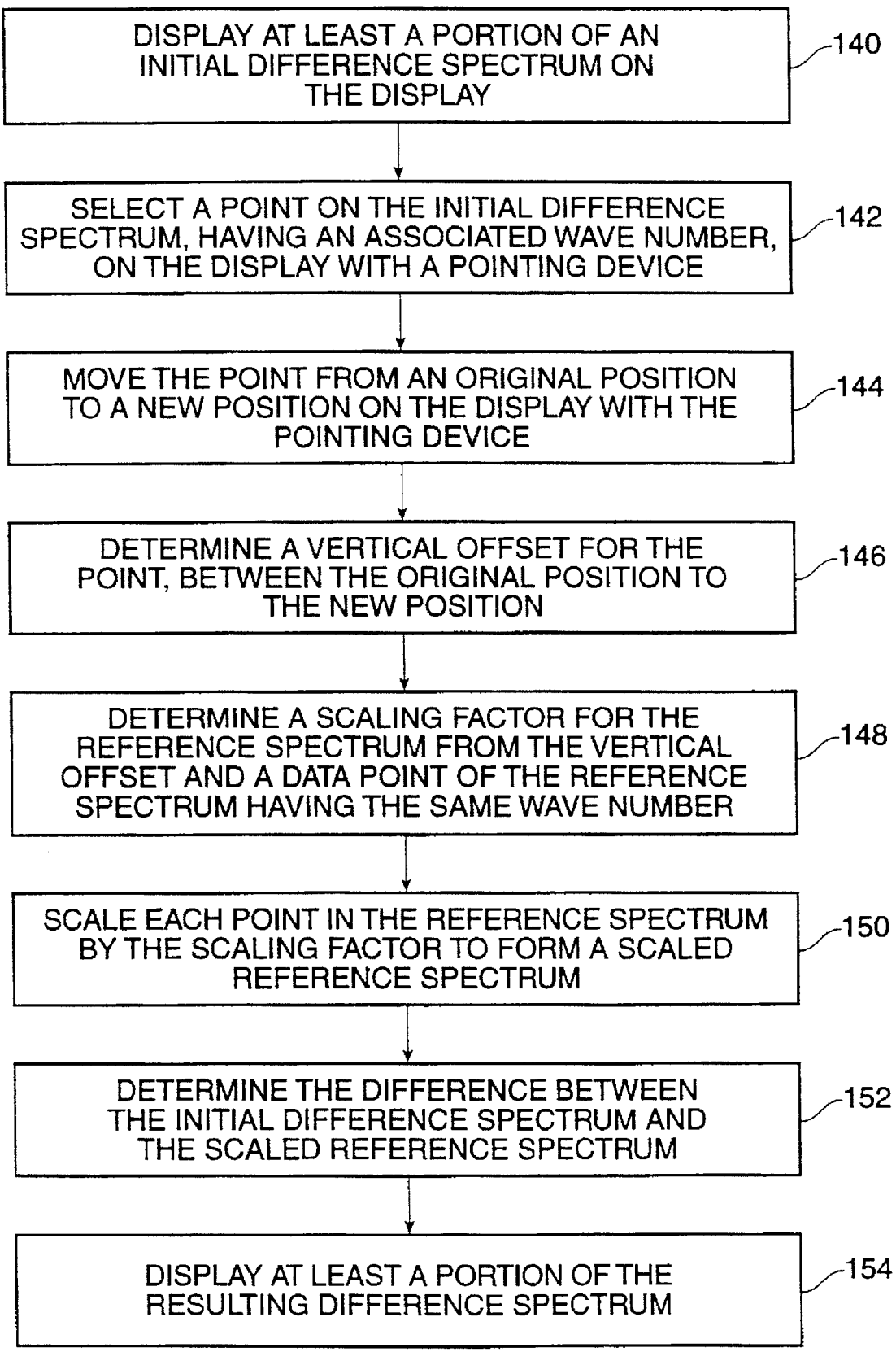
FIG. 8 is a flow diagram of an embodiment of the process of forming a difference spectrum.

FIG. 8 is a flow diagram of an embodiment of the process of forming a difference spectrum. At least a portion of an initial difference spectrum is first displayed to the user on the display (step 140). In one embodiment, the initial difference spectrum is equal to the sample spectrum, i.e., the values of "a" and "b" in equation (1) are zero (0). Alternatively, the initial difference spectrum can be proportional or linearly related to the sample spectrum. The user selects a point on the initial difference spectrum with a pointing device, such as mouse 5 (step 142). The selected point represents a data point in the initial difference spectrum having an absorbance value at an associated wave number. The user moves the point from the original position to a new position, again using mouse 5 in a well known manner (step 144). The processor then determines the vertical offset between the original position and the new position (step 146). In the preferred embodiment the difference in absorbance values between the original position to the new position is represented by the vertical offset.

A scaling factor for the reference spectrum is determined based upon the value of the vertical offset and upon the value of the reference spectrum at the wavenumber of the selected point (step 148). In one embodiment, the scaling factor is the difference in absorbance values divided by the absorbance value of the reference spectrum at the wave number. The reference spectrum is then uniformly scaled by the scaling factor to form a scaled reference spectrum (step 150).

In one embodiment, the absorbance value for each data point in the reference spectrum is multiplied by the scaling factor to form the scaled reference spectrum. The processor then determines the difference between the sample spectrum and the scaled reference spectrum (step 152). In one embodiment, for each wave number, the absorbance value for the sample spectrum is subtracted by the absorbance value for the scaled reference spectrum to form the difference spectrum. At least a portion of the resulting difference spectrum is then displayed to the user (step 154), and the resulting difference spectrum will run through the new position of the selected point. The display of the difference spectrum, in a preferred embodiment, serves as immediate feedback to the user of the results of the subtraction process. The user may repeatedly perform steps 140–154 using the difference spectrum in place of the sample spectrum, to rescale and resubtract the reference spectrum from the difference spectrum and to form a new difference spectrum.

In some situations, the reference spectrum or the sample spectrum contain a baseline offset. When performing the above described steps, when the reference spectrum is scaled, the scaled reference spectrum also contains a baseline offset. Subtracting the scaled reference spectrum from the sample spectrum would then result in a difference spectrum having a non-zero baseline offset. Although a non-zero baseline offset does not interfere with qualitative results of the subtraction, the offset of the sample spectrum may be visually distracting to the user. To address this issue, in a preferred embodiment of the present invention, when the scaling factor "a" is determined, the offset factor "b" is also determined such that for each difference spectrum, the baseline offset will be approximately zero.

Figure 9:
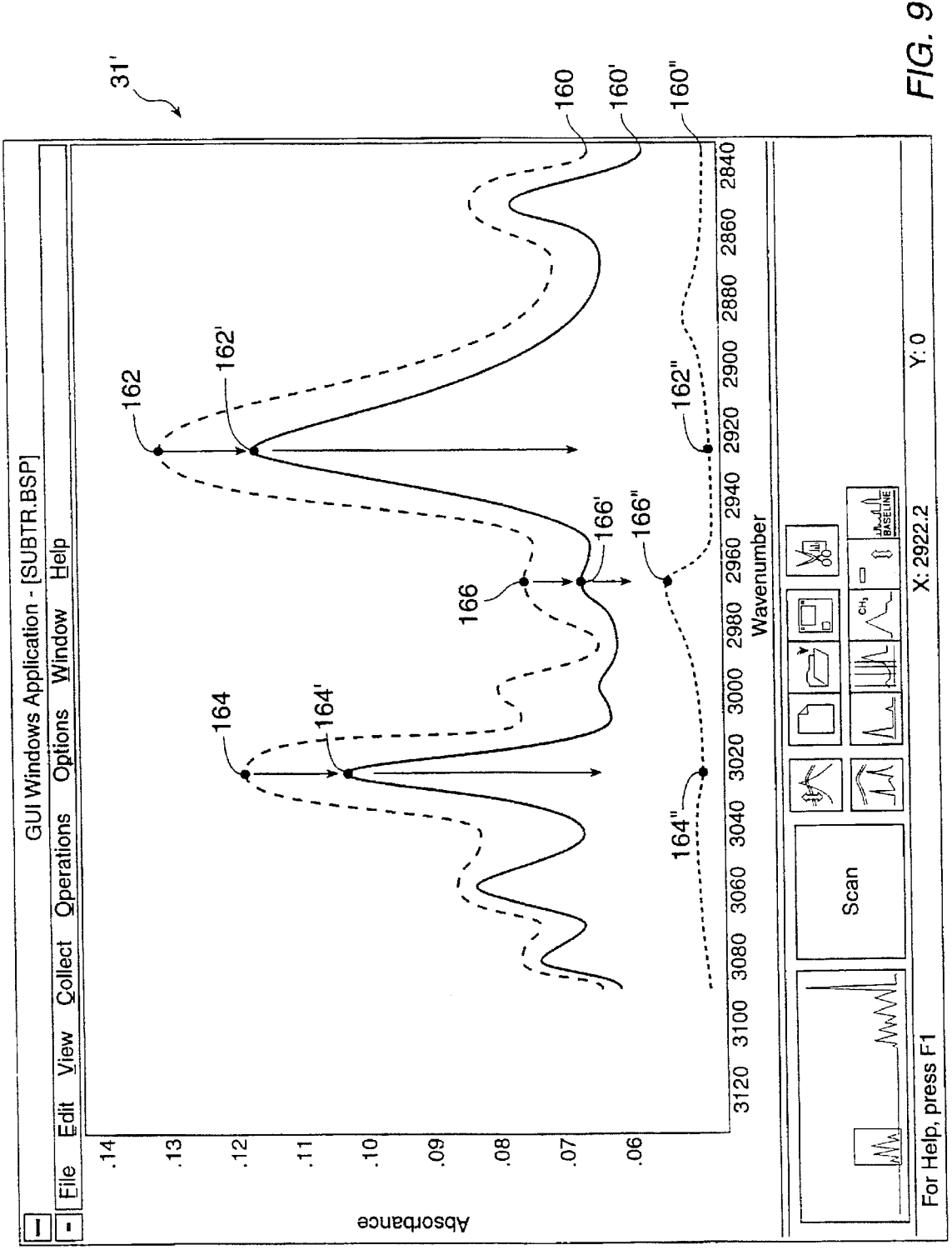
FIG. 9 illustrates a display of a portion of an initial difference spectrum and portions of two representative difference spectrum.

FIG. 9 illustrates a display of a portion 160 of an initial difference spectrum (not shown in its entirety) and portions 160, 160', and 160" of three representative difference spectra (not shown in their entirety) on a detailed window 31'. Portion 160 includes points 162, 164, 166, portion 160' includes points 162', 164', and 166', and portion 160" includes points 162", 164", and 166".

In a preferred embodiment, the initial difference spectrum is set equal to the sample spectrum. The initial difference spectrum is equal to the sample spectrum without the reference spectrum being subtracted. To calculate a new difference spectrum the user uses mouse 5 to select a point on the initial difference spectrum. The user then moves that point vertically on the display. Moving the point on the initial difference spectrum vertically is equivalent to subtracting a scaled percentage of the reference spectrum from the sample spectrum.

Portion 160 illustrates an initial difference spectrum. When a user selects and drags point 162 to point 162', for example, Portion 160 is erased and portion 160' is displayed to the user. Of course multiple intermediate difference spectra are also displayed to the user as the user moves from 162 to 162'. These are not shown, for clarity. The user continues dragging data points until the user is satisfied with the difference spectrum, for example, 160".

FIG. 9 illustrates the result of the user dragging point 162 of portion 160 to point 162' and onto point 162". In a preferred embodiment, only one difference spectrum is displayed to the user at a time, e.g., 160, 160', or 160". In response to the vertical offset between point 162 to 162' and onto 162", the processor calculates the remaining points in the difference spectrum, as illustrated by portion 160' and 160". In a preferred embodiment, if the baseline offset of the reference spectrum is zero, the baseline compensation factor "b", in equation (1), is set to zero. Equation (1) then simplifies to equation (2).

$$Z=S-(a*R) \quad (2)$$

In equation (2), Z represents the difference spectrum, S represents the sample spectrum, R represents the reference spectrum, and "a" is the scaling factor for the reference spectrum. In FIGS. 7 and 9, the value of point 162' corresponds to Z, the point 162 corresponds to S, and point 132 corresponds to R for a given wave number. Since the processor knows the values for Z, S, and R, the processor calculates a corresponding value for "a" based upon point 122'. Using this value for "a" and knowing the values of the sample spectrum S and reference spectrum R for the remaining wave numbers, the processor then calculates the remaining values for the difference spectrum Z for all the remaining wave numbers.

In FIG. 7, for example, point 122 has an absorbance of about 0.132 and point 132 has an absorbance of about 0.137, and in FIG. 9, point 162' has an absorbance of about 0.102.

Using equation (2) with Z=0.102, S=0.132, and R=0.137, the scaling factor "a" is calculated to be about 0.219.

Using 0.219 for "a" in equation (2), the processor then calculates the difference spectrum for each of the remaining points from the sample spectrum. For example in FIG. 7, point 124 has an absorbance of about 0.119 and point 134 has an absorbance of about 0.125. Using equation (2) with S=0.119, "a"=0.219 as calculated above, and R=0.125, the value of point 164' is calculated to be about 0.916. Point 164' in FIG. 9 is thus set to 0.916. In a preferred embodiment, the described sequential operations appear continuous.

In a preferred embodiment, the user graphically manipulates points upon the difference spectrum, until satisfied that difference spectrum does not include any contributions from the reference spectrum. As illustrated in FIG. 9, by maintaining a baseline offset for the difference spectrum that is approximately zero, once the absorbance of the difference spectrum has reached a relatively constant value, the user can then identify peaks such as point 166". Point 166" may represent another chemical component in the sample spectrum, for example.

The difference spectrum can be displayed and manipulated in its own window. The sample spectrum and the reference spectrum may or may not be displayed to the user, and if so may be displayed in another window. For example, the difference spectrum and the sample spectrum may be displayed in windows 31 and 30, respectively, as in FIG. 6. Alternatively, all three spectrum can be displayed in a single window.

The user repeats the above graphic subtraction procedure with a new reference spectrum from a library of reference spectra in order to identify any remaining components or to remove other artifacts on the difference spectrum.

Spectral Searching

FIG. 10 illustrates the result of searching the sample spectrum in FIG. 2 against a library of known spectrum. The results, stored in component box 170 are displayed to the user and can be saved to memory. In a preferred embodiment, component box 170 includes a name column 172, a spectrum column 174, and a structure column 176. Other information related to the spectral information contained in each row may be stored in other columns.

In the preferred embodiment, the processor automatically compares the sample spectrum to a library of reference spectra stored in disk drive 9 to determine the composition of the sample spectrum. The processor determines the composition according to well known algorithms known to one skilled in the art.

In a preferred embodiment, after determining the composition of the sample spectrum, the processor displays the name of the reference samples matched, a full scale view of the reference spectrum, and displays the chemical structure. In FIG. 10, the samples are stored in name column 172, the reference spectrum for the chemicals are shown in spectrum column 174, and the structure of the chemicals are shown in structure column 176.

Graphic Manipulation—Baseline Offset Correction

Baseline Offsets are used to compensate for offsets in absorbance values due to artifacts during collection of the sample spectrum or due to artifacts in subtracting reference spectrum. If an offset is relatively constant throughout the range of wave numbers of the sample spectrum, the value of "b" in equation (1) can be set to a constant to correct the offset. However, if an offset is non-uniform throughout the range of wave numbers of the sample spectrum, the user can define a baseline offset as a function of wavenumber to correct the offset. When correcting only the baseline offset, the value of "a" in equation (1) is preferably set to zero and the value of "b" is modified.

In a preferred embodiment the user directly sets the value of "b" in equation (1) to a constant in two ways. First, when in graphic subtraction mode, the user can directly select a value for "b" by commonly used techniques such as entering text in a dialog box, or scrolling through a list of values of "b" with up and down arrows on the display (while "a" is held constant). Second, when in a baseline correction mode, the user can graphically set the value of "b" to a constant. The user enters the baseline correction mode by selecting command button 62.

FIGS. 11 and 12 illustrate the definition of a portion of a baseline offset (not shown) as a function of wavenumber and the resulting spectrum. The baseline offset includes line segments 180 and 182 and curved segment 184.

In a preferred embodiment, the user directly sets the value of "b" in equation (1) as a function of wavenumber while in the base line correction mode. In operation, the user graphically defines the shape of the baseline offset in relation to the wavenumber with mouse 5. Using well known graphic manipulation techniques from computer drawing programs, the user can define line or curved segments by defining the appropriate parameters as shown as line segments 180 and 182 and as curved segment 184. In a preferred embodiment, immediately after editing the graphic baseline offset, the sample spectrum is updated to reflect the new baseline offset. This is illustrated in FIG. 12 with the baseline correction of FIG. 11 of the sample spectrum in FIG. 2.

Graphic Manipulation Based upon Regions of Interest

Regions of Interest (ROI) are areas in a spectrum upon which the processor utilizes spectrum data for operations.

FIG. 13A illustrates a display of a portion 190 of a spectrum on detailed window 30. Portion 190 is a portion of the difference spectrum including a region of interest (RO) 200.

In operation, selecting command button 78 in FIG. 2 allows the user to define an ROI. The user defines an ROI by first delineating a wavenumber range of the spectrum and choosing whether the delineated range is the ROI, or the spectrum outside the delineated range is the ROI.

In a preferred embodiment, without an ROI 200, spectral searching of a sample spectrum and a reference spectra is calculated based upon the entire range of wave numbers as illustrated in FIG. 11. In a preferred embodiment, with an ROI 200, spectral searching is calculated based only upon the range of wave numbers in the defined ROI 200. The spectral searching occurs over the entire wavenumber range as without ROI 200, however, ROI 200 is the only region from which the processor analyzes data. An application where an ROI is used is when the composition of only a certain portion of the sample spectrum is of interest.

FIG. 13B illustrates the result of an spectral searching based upon ROI 200. In contrast to the result of the spectral searching in FIG. 10, the spectral searching in FIG. 13B results in locating only a particular substance.

Other Features

FIG. 14 illustrates retrieving a previously scanned sample spectrum from disk drive 9. A dialog box 200 includes a file box 210 a text entry box 220, a preview box 230, and a retrieve button 240.

In a preferred embodiment, the user selects buttons 73 or 74 to open dialog box 200 on display 2. The list of files, directories and drives, either local or on a network accessible machine, is displayed in file box 210. The user selects a file to retrieve from the list of files in file box 210 by using a graphical input device, such as mouse 5, and pointing and clicking upon the file name. Alternatively, the user selects a file to retrieve by typing a file name into keyboard 4, after first selecting text entry box 220 with mouse 5. A preview of the user selected file is displayed in preview box 230 when the user clicks upon the file name, or enters a file name into text entry box 220. Once the user is satisfied with the file selection, the user retrieves the spectrum data by pointing and double clicking upon the file name with mouse 5, or clicking upon retrieve button 240.

In a preferred embodiment, a file (or document) contains data (a spectrum) for a sample or a reference, or a series of spectra, or spectra from different samples, or spectra processed in different ways, plus other information related to the spectrum. This typically includes data from an experiment, an individual's work, a series of related experiments, a day's worth of work, a project, etc.

The presentation of the document by the software is in one window. A moveable "window shade" lines separates the window into two portions: one containing a large area for the presentation of spectra and the second containing a "spreadsheet". This "spreadsheet" format for the data provides a environment familiar to the user for presenting data to the user. Each row in the spreadsheet contains cells displaying information related to a single spectrum, possibly including but not limited to properties such as the name of the spectrum, the spectrum trace itself, text information about the sample or spectrum, the chemical structure of the material, etc. Each column of the spreadsheet is dedicated to a particular spectrum property. The selection of spreadsheet columns is user configurable.

To modify or view a document, the user is given the ability to manipulate the data in a manner similar to spreadsheets. A typical display of a document displays the names of the spectra/traces in one column of the document, the actual spectra/traces in another column of the document, the properties of the underlying samples in another column of the document and other graphic information in yet another column of the document. One example of a view of a document is illustrated in FIG. 10. Graphic information includes chemical structures as illustrated in column 176 of FIG. 10.

Figure 21:
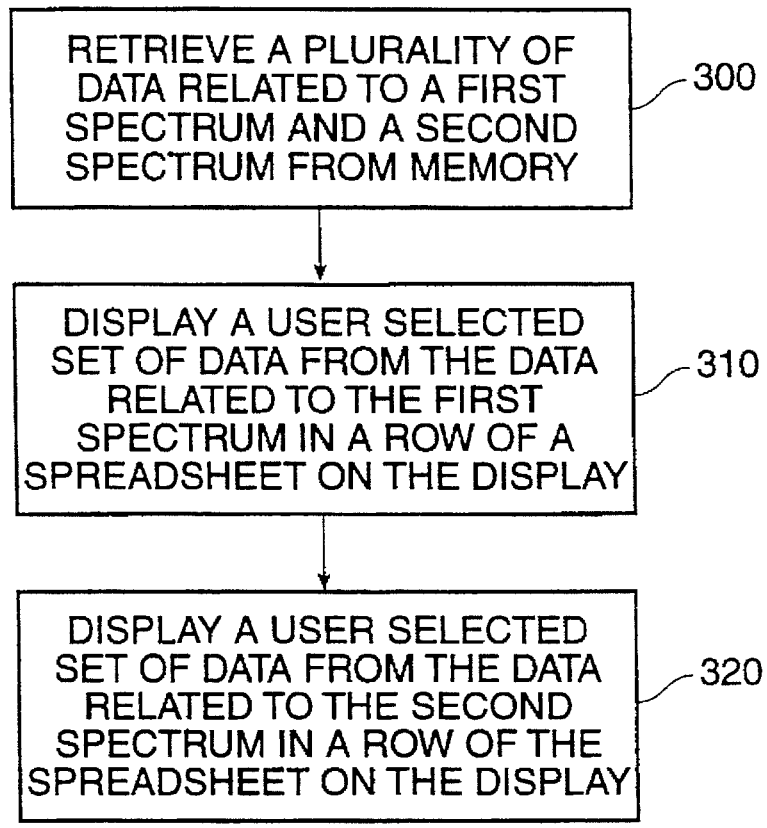
FIG. 21 is a flow diagram of one embodiment of the process of displaying a user selected set of data from a first and a second spectrum including spectrum traces in rows of a spreadsheet.

FIG. 21 is a flow diagram of one embodiment of the process of displaying a user selected set of data from a first and a second spectrum including spectrum traces in rows of a spreadsheet. Initially the user retrieving a plurality of data related to a first spectrum and a plurality of data second spectrum from the plurality of spectra from the memory (step 300). This data is typically stored in the same file. In the next step, a user selected set of data from the plurality of data related to the first spectrum, that includes a spectrum trace for the first spectrum, is displayed on the display (step 310). As illustrated in the examples below, the data is displayed in a first row of a "spreadsheet" on the display. Then, a user selected set of data from the plurality of data related to the second spectrum, that includes a spectrum trace for the second spectrum, is displayed on the display (step 320). The data is displayed in a second row of the "spreadsheet" on the display.

The interface allows the user to access individual spectra/traces, ranges or particular spectra/traces, or groups of spectra/traces in a document or between documents, and allows the user to align or register spectra that span different ranges. The interface also allows the user to choose which columns of a document to display at any one time. Such a choice is variable between documents and between applications.

The ability to align spectra/traces is important where a series of traces are displayed in a spreadsheet column having corresponding data points (e.g. wavenumber) in the traces, whether the spectra have common range or not. In one embodiment, all spectra in a spreadsheet with common X axis units are displayed each scaled separately to display its full extent. In another embodiment, all spectra having a common range of wavenumbers, for example, are displayed using the same display range limits and same range scale. Selecting a spectrum by clicking in the spectrum's trace display cell causes that spectrum to be shown with the full extent of its data range, and causes all other spectra displayed in that specific spreadsheet view that share X units with the selected spectrum to also be displayed with that same extent. In an alternative embodiment, the displays of spectra are rescaled to the extent required to show the full x range of all spectrum sharing common X units.

Figure 22:
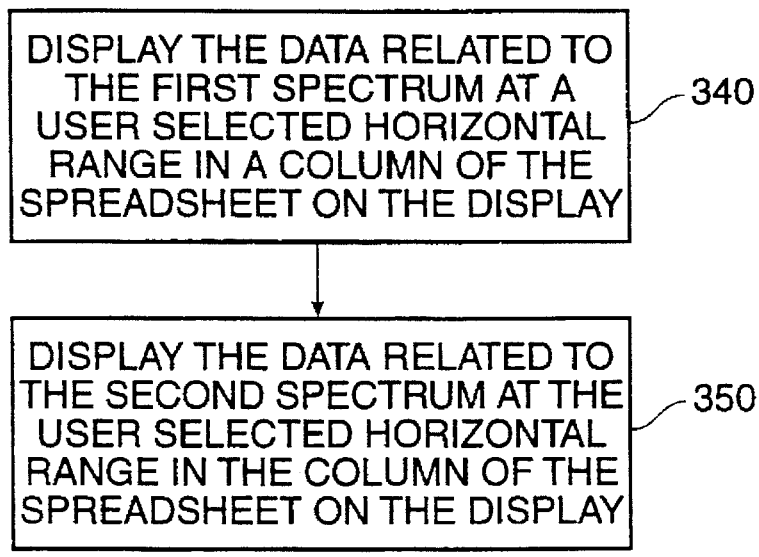
FIG. 22 is a flow diagram of one embodiment of the process of displaying a user selected set of data from a first and a second spectrum including spectrum traces at a user selected horizontal range in columns of a spreadsheet.

FIG. 22 is a flow diagram of one embodiment of the process of displaying a user selected set of data from a first and a second spectrum including spectrum traces at a user selected horizontal range in columns of a spreadsheet. In addition to the steps illustrated in FIG. 21, the spectrum trace for the first spectrum is displayed at a user selected horizontal range in a column of the spreadsheet on the display (step 340) and the spectrum trace for the second spectrum is displayed at the user selected horizontal range in the column of the spreadsheet on the display (step 350).

Figure 16:
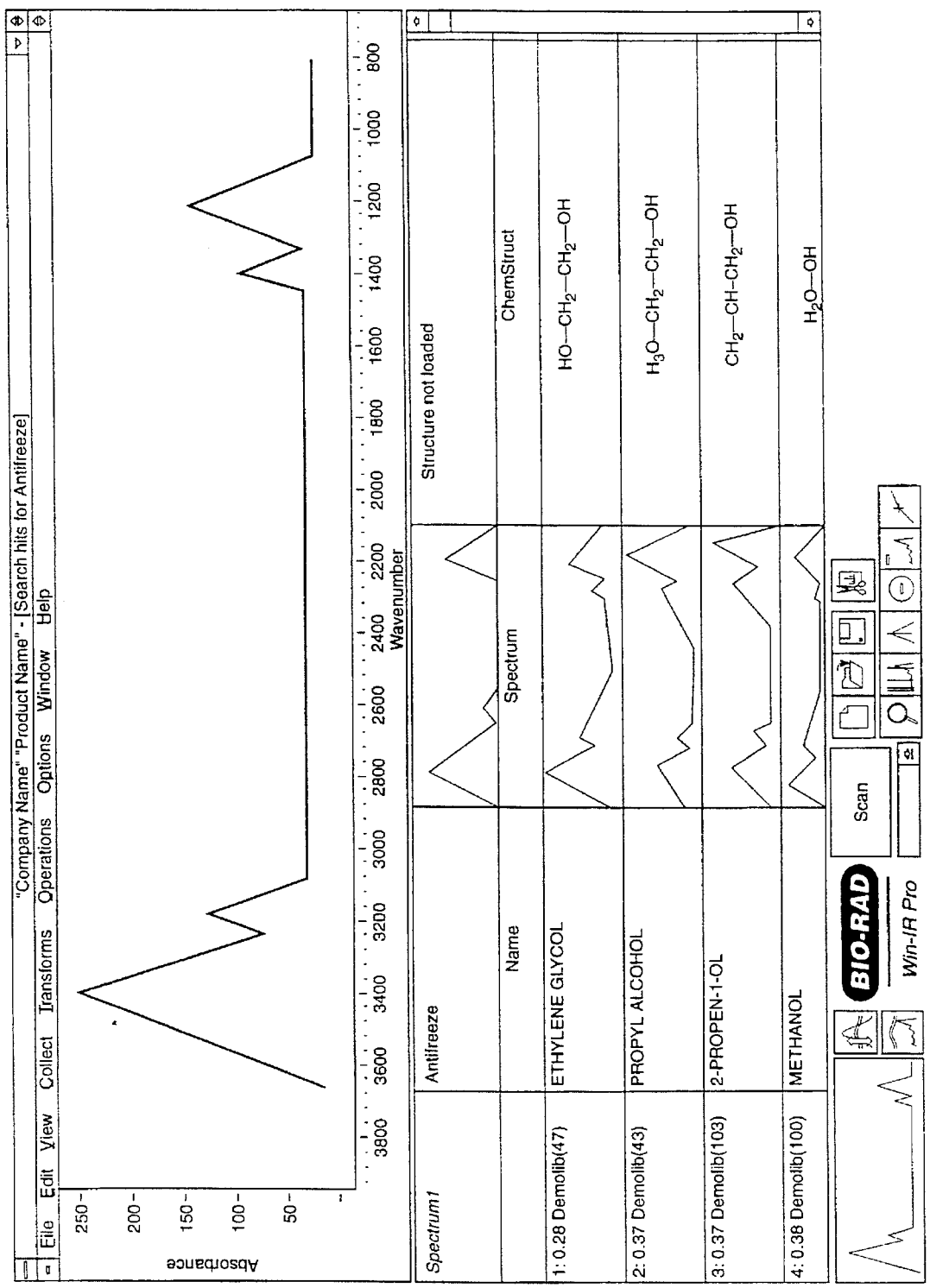
FIG. 16 illustrates a document containing a spectral library that includes names and index information for the spectrum, the actual spectrum, and properties and structures of the compounds.

Examples of the information stored in documents include:

1) A document containing a spectral library that includes names and index information for the spectrum, the actual spectrum, and properties and structures of the compounds. This is illustrated in FIG. 16.

Figure 17:
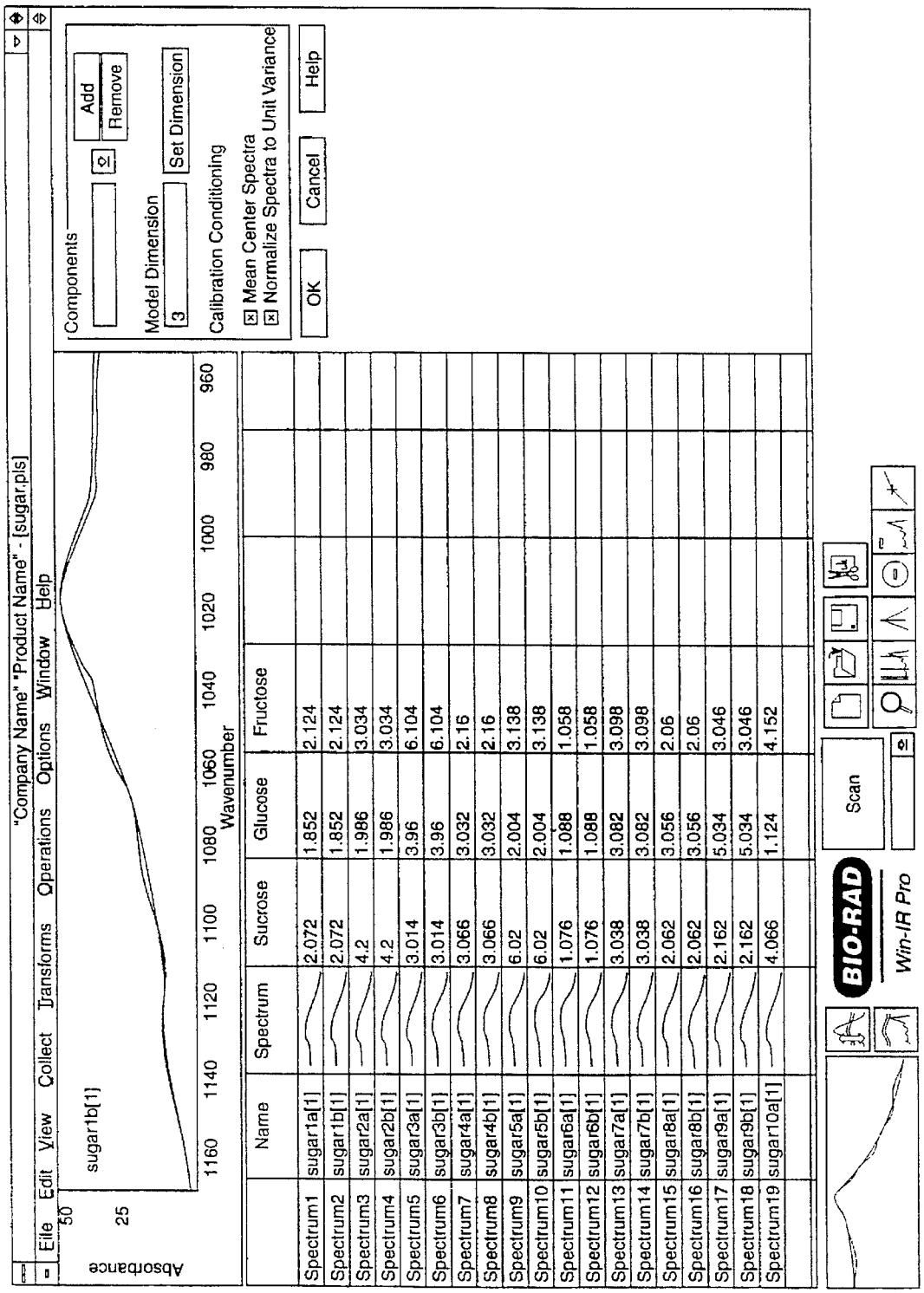
FIGS. 17 and 18 illustrates a document containing a collection of spectrum used to set up and calibrate quantitative analysis.
Figure 18:
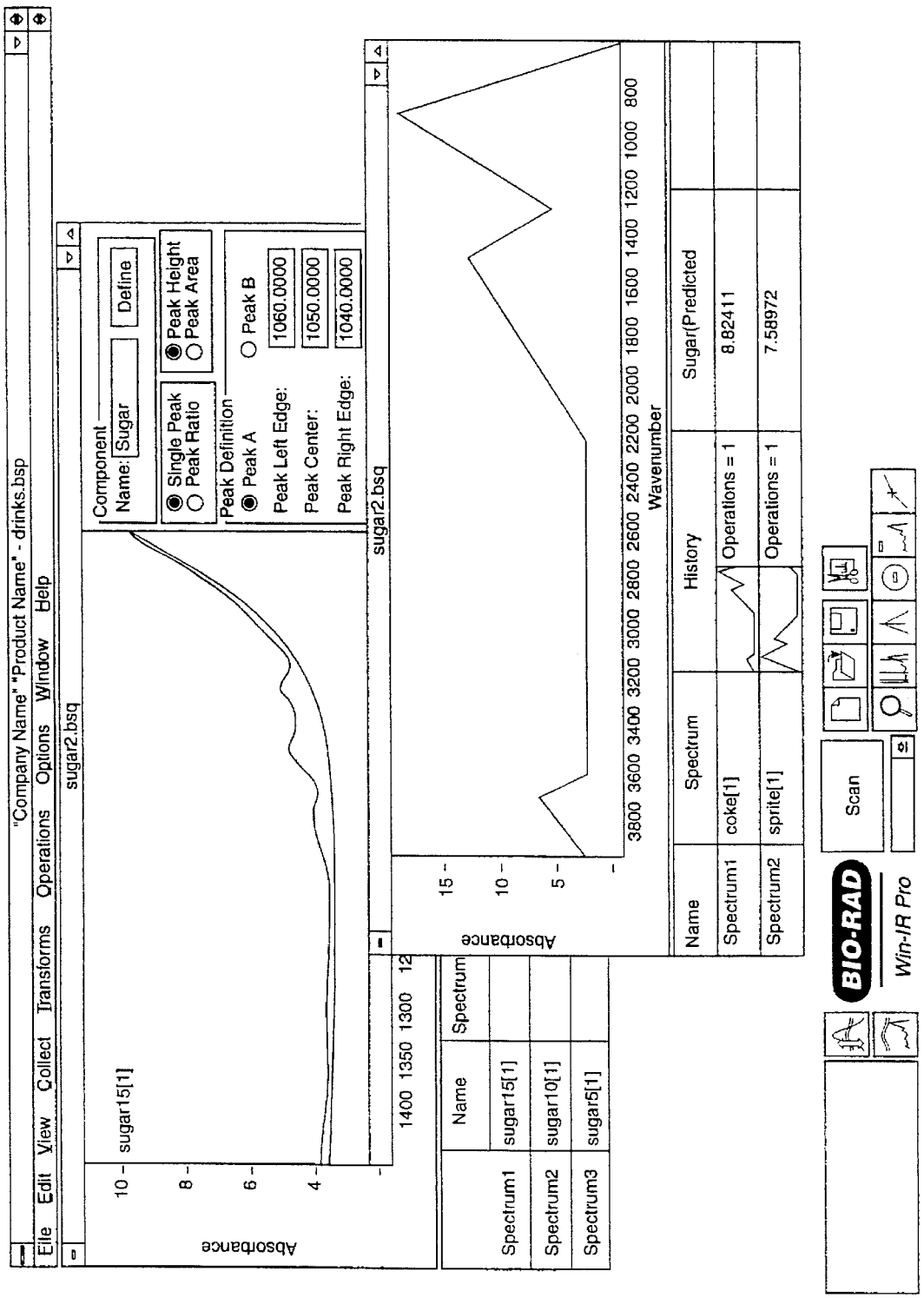

2) A document containing a collection of spectrum used to set up and calibrate quantitative analysis. For example, a document that contains the actual spectrum of the specimens, the names of the components present in each specimen, the concentrations of those components in each specimen, the portion(s) of the spectrum to be used in the calibration and analysis, the style of analysis (e.g. band height measurement, partial least squares analysis), and the resulting calibration data. This is illustrated in FIG. 17 and FIG. 18.

Figure 19:
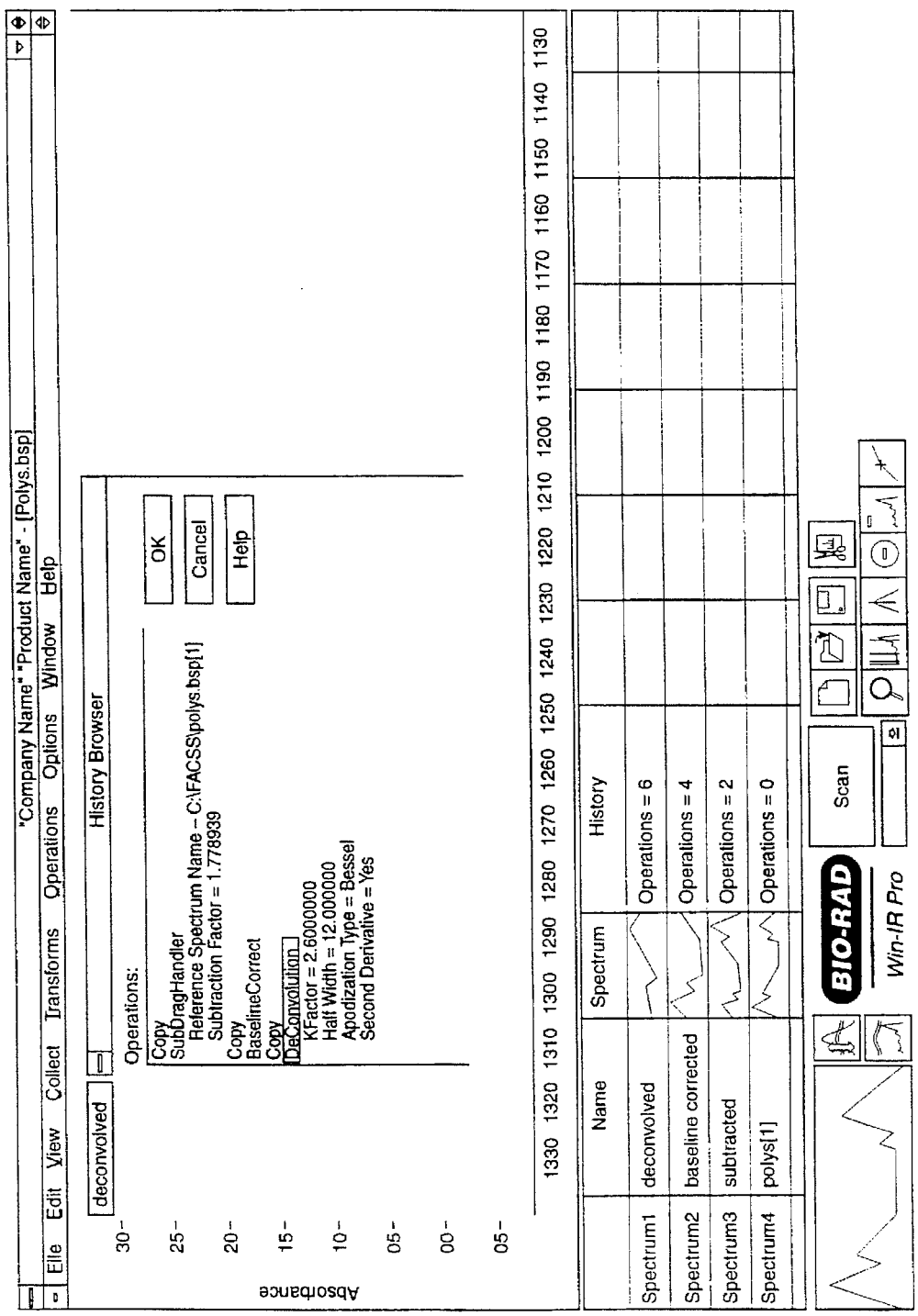
FIG. 19 illustrates a document containing a processing history.

3) A document containing a collection of spectrum to be analyzed. For example, a document that contains spectrum to be analyzed, the resulting components and component concentration present in each spectrum, the method used for the analysis, and the processing history. This is illustrated in FIG. 19.

4) A document containing a set of spectrum from an infrared mapping experiment. For example, spectrum that are associated with coordinates from which the spectrum was obtained, and data obtained from the set of spectrum that produce infrared-based maps of the specimen.

5) A document containing a set of spectrum collected under varying conditions. For example, different experimental conditions and the associated data. Conditions include those internal to the spectrometer (e.g. resolution, number of scans), and external to the spectrometer (e.g. temperature of the specimen, pressure). Alternatively, the software may itself control those conditions.

Figure 20:
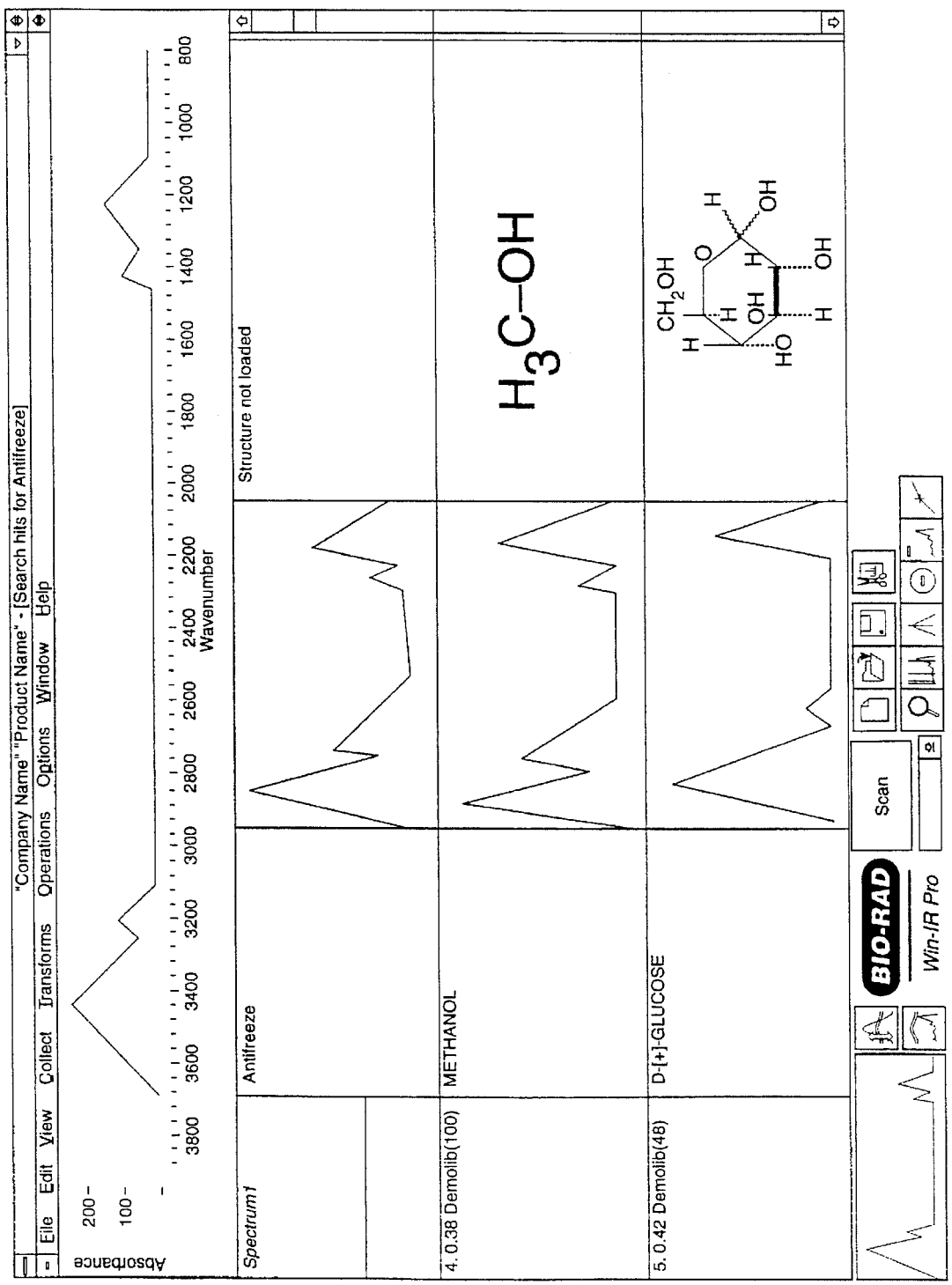
FIG. 20 illustrates a document containing the results of a spectral search.

FIG. 20 illustrates a document containing both the results of a spectral search as well as the sample spectrum.

FIG. 15 illustrates the peak mode. As will be described below, the peak mode allows the user to quickly obtain characteristics of a selected peak.

In a preferred embodiment, selecting command button 79 in FIG. 2 enters the system into a "peak" mode. In peak mode the user uses mouse 5 to select a point such as point 53 on partial spectrum 51. In response to the selection, the processor automatically determines characteristics of the closest peak, such as peak 54. These characteristics can include the maximum and minimum absorptions of the peak, the wavenumber of the peak, the area of the peak, the range of wave numbers for the peak.

Conclusion

In the foregoing specification, the invention has been described with reference to a specific exemplary embodiments thereof. Many changes or modifications are readily envisioned. For example, changing the graphical manipulation from that of equation (1), changing the effect of the graphical manipulation based upon direction of movement, and including further functional buttons on the display, among other changes, are included within other embodiments of the present invention.

The specification and drawings are, accordingly, to be regarded in an illustrative rather than in a restrictive sense. It will, however, be evident that various modifications and changes may be made thereunto without departing from the broader spirit and scope of the invention as set forth in the claims.

What is claimed is:

1. A method of displaying a plurality of data related to a plurality of spectra on a computer system, the computer system including a display and a memory, the method comprising the steps of:

retrieving a plurality of data related to a first spectrum and a plurality of data related to a second spectrum from the plurality of spectra from the memory;

displaying a user-selected set of data from the plurality of data related to the first spectrum including a spectrum trace for the first spectrum, in a first row of a spreadsheet on the display;

displaying a user-selected set of data from the plurality of data related to the second spectra including a spectrum trace for the second spectrum, in a second row of the spreadsheet on the display.

2. The method of claim 1, wherein the first spectrum displaying step further comprises the step of displaying the spectrum trace for the first spectrum at a user-selected horizontal range in a column of the spreadsheet on the display; and wherein the second spectrum displaying step further comprises the step of displaying the spectrum trace for the second spectrum at the user-selected horizontal range in the column of the spreadsheet on the display.

3. The method of claim 2, wherein the first spectrum displaying step further comprises the step of displaying the spectrum trace for the first spectrum at a user-selected horizontal scale; and wherein the second spectrum displaying step further comprises the step of displaying the spectrum trace for the second spectrum at the user-selected horizontal scale.

4. The method of claim 1, wherein the first spectrum displaying step further comprises the step of displaying a full range of the spectrum trace for the first spectrum in a column of the spreadsheet on the display; and wherein the second spectrum displaying step further comprises the step of displaying a full range of the spectrum trace for the second spectrum in the column of the spreadsheet on the display.

5. The method of claim 1, wherein the first spectrum displaying step further comprises the step of displaying at least a portion of the spectrum trace for the first spectrum in a column of the spreadsheet on the display; and wherein the second spectrum displaying step further comprises the step of displaying at least a portion of the spectrum trace for the second spectrum in the column of the spreadsheet on the display, wavenumbers of the portion of the spectrum trace for the second spectrum aligned with wavenumbers of the portion of the spectrum trace for the first spectrum.

6. An apparatus for displaying a plurality of data related to a plurality of spectra on a computer system, the computer system including a memory, the apparatus further comprising:

a processor for retrieving a plurality of data related to a first spectrum and a plurality of data related to a second spectrum from the plurality of spectra from the memory;

a display configured to display a user-selected set of data from the plurality of data related to the first spectrum including a spectrum trace for the first spectrum, in a first row of a spreadsheet, and configured to display a user-selected set of data from the plurality of data related to the second spectra including a spectrum trace for the second spectrum, in a second row of the spreadsheet.

7. The apparatus of claim 6, wherein the display is also configured to display the spectrum trace for the first spectrum at a user-selected horizontal range in a column of the spreadsheet; and wherein the display is also configured to display the spectrum trace for the second spectrum at the user-selected horizontal range in the column of the spreadsheet.

8. The apparatus of claim 6, wherein the display is also configured to display the spectrum trace for the first spectrum at a user selected horizontal scale; and wherein the display is also configured to display the spectrum trace for the second spectrum at the user selected horizontal scale.

9. The apparatus of claim 6, wherein the display is also configured to display a full range of the spectrum trace for the first spectrum in a column of the spreadsheet on the display; and wherein the display is also configured to display a full range of the spectrum trace for the second spectrum in the column of the spreadsheet on the display.

10. The apparatus of claim 6, wherein the display is also configured to display at least a portion of the spectrum trace for the first spectrum in a column of the spreadsheet on the display; and wherein the display is also configured to display at least a portion of the spectrum trace for the second spectrum in the column of the spreadsheet on the display, wavenumbers of the portion of the spectrum trace for the second spectrum aligned with wavenumbers of the portion of the spectrum trace for the first spectrum.

11. A computer system for displaying a plurality of data related to a plurality of spectra on a computer system, the computer system including a display, the computer system further comprising:

a memory storage device including:

code that directs a processor to retrieve a plurality of data related to a first spectrum and a plurality of data related to a second spectrum from the plurality of spectra;

code that directs the display to display a user-selected set of data from the plurality of data related to the first spectrum including a spectrum trace for the first spectrum, in a first row of a spreadsheet; and code that directs the display to display a user-selected set of data from the plurality of data related to the second spectra including a spectrum trace for the second spectrum, in a second row of the spreadsheet.

12. The apparatus of claim 11, wherein the memory storage device also includes:

code that directs the display to display the spectrum trace for the first spectrum at a user-selected horizontal range in a column of the spreadsheet; and code that directs the display to display the spectrum trace for the second spectrum at the user-selected horizontal range in the column of the spreadsheet.

13. The apparatus of claim 11, wherein the memory storage device also includes:

code that directs the display to display the spectrum trace for the first spectrum at a user selected horizontal scale; and code that directs the display to display the spectrum trace for the second spectrum at the user selected horizontal scale.

14. The apparatus of claim 31, wherein the memory storage device also includes:

code that directs the display to display a full range of the spectrum trace for the first spectrum in a column of the spreadsheet on the display; and code that directs the display to display a full range of the spectrum trace for the second spectrum in the column of the spreadsheet on the display.

15. The apparatus of claim 11, wherein the memory storage device also includes:

code that directs the display to display at least a portion of the spectrum trace for the first spectrum in a column of the spreadsheet on the display; and code that directs the display to display at least a portion of the spectrum trace for the second spectrum in the column of the spreadsheet on the display, wavenumbers of the portion of the spectrum trace for the second spectrum aligned with wavenumbers of the portion of the spectrum trace for the first spectrum.

16. A method for displaying data associated with a spectrum on a computer system, the computer system including a display and a memory, the method comprising the steps of:

retrieving a first plurality of data associated with the spectrum and a second plurality of data associated with the spectrum from the memory;

displaying a first set of data from the first plurality of data, including a first spectrum trace, in a first row and a column of a spreadsheet on the display; and displaying a second set of data from the second plurality of data, including a second spectrum trace, in a second row and the column of the spreadsheet on the display.

17. A computer program product for displaying data related to spectra on a computer system, the computer program product comprising:

a memory storage device including:

code that directs a processor to retrieve data related to a first spectrum and data related to a second spectrum from the spectra;

code that directs a display to display a user-selected set of data from the data related to the first spectrum including a spectrum trace for the first spectrum, in a first row of a spreadsheet; and code that directs the display to display a user-selected set of data from the data related to the second spectrum including a spectrum trace for the second spectrum, in a second row of the spreadsheet.

18. The computer program product of claim 17, wherein the memory storage device also includes:

code that directs the display to display the spectrum trace for the first spectrum at a user-selected horizontal range in a column of the spreadsheet; and code that directs the display to display the spectrum trace for the second spectrum at the user-selected horizontal range in the column of the spreadsheet.

19. The computer program product of claim 17, wherein the memory storage device also includes:

code that directs the display to display the spectrum trace for the first spectrum at a user selected horizontal scale; and code that directs the display to display the spectrum trace for the second spectrum at the user selected horizontal scale.

20. The computer program product of claim 17, wherein the memory storage device also includes:

code that directs the display to display a full range of the spectrum trace for the first spectrum in a column of the spreadsheet on the display; and code that directs the display to display a full range of the spectrum trace for the second spectrum in the column of the spreadsheet on the display.

21. The computer program product of claim 17, wherein the memory storage device also includes:

code that directs the display to display at least a portion of the spectrum trace for the first spectrum in a column of the spreadsheet on the display; and code that directs the display to display at least a portion of the spectrum trace for the second spectrum in the column of the spreadsheet on the display, wavenumbers of the portion of the spectrum trace for the second spectrum aligned with wavenumbers of the portion of the spectrum trace for the first spectrum.

* * * * *